US009482588B2

(12) United States Patent
Persson et al.

(10) Patent No.: US 9,482,588 B2
(45) Date of Patent: Nov. 1, 2016

(54) METHOD AND APPARATUS FOR EVALUATING CLAMP FORCE IN A BOLT BY MEANS OF ULTRA-SONIC MEASUREMENTS

(71) Applicant: ATLAS COPCO INDUSTRIAL TECHNIQUE AB, Stockholm (SE)

(72) Inventors: Erik Vilhelm Persson, Solna (SE); Arne Torgny Roloff, Stockholm (SE)

(73) Assignee: ATLAS COPCO INDUSTRIAL TECHNIQUE AB, Stockholm (SE)

(*) Notice: Subject to any disclaimer, the term of this patent is extended or adjusted under 35 U.S.C. 154(b) by 0 days.

(21) Appl. No.: 14/651,881

(22) PCT Filed: Dec. 10, 2013

(86) PCT No.: PCT/EP2013/076008
§ 371 (c)(1),
(2) Date: Jun. 12, 2015

(87) PCT Pub. No.: WO2014/095471
PCT Pub. Date: Jun. 26, 2014

(65) Prior Publication Data
US 2015/0316435 A1 Nov. 5, 2015

(30) Foreign Application Priority Data
Dec. 18, 2012 (SE) ........................ 1251445

(51) Int. Cl.
*F16B 31/02* (2006.01)
*G01L 5/24* (2006.01)
(Continued)

(52) U.S. Cl.
CPC ............. *G01L 5/246* (2013.01); *B25B 23/147* (2013.01); *G01L 1/255* (2013.01); *G01L 5/0042* (2013.01); *F16B 31/02* (2013.01); *G01L 5/24* (2013.01); *G01N 2291/2691* (2013.01)

(58) Field of Classification Search
CPC .. F16B 2031/022; F16B 31/02; G01L 1/255; G01L 5/0042; G01L 5/24; G01L 5/246; G01N 2291/011; G01N 2291/02827; G01N 2291/02854; G01N 2291/2691
USPC ............. 73/581, 597, 602, 627, 761, 862.21
See application file for complete search history.

(56) References Cited

U.S. PATENT DOCUMENTS 5,216,622 A * 6/1993 Kibblewhite ........... G01L 5/246
700/275
6,116,094 A * 9/2000 Andersson .............. G01L 1/255
324/635
(Continued)

FOREIGN PATENT DOCUMENTS

WO 2004027271 A2 4/2004

OTHER PUBLICATIONS

International Search Report (ISR) and International Preliminary Report on Patentability (IPRP) dated Jun. 12, 2014 issued in International Application No. PCT/EP2013/076008.

*Primary Examiner* — Lisa Caputo
*Assistant Examiner* — Jonathan Dunlap
(74) *Attorney, Agent, or Firm* — Holtz, Holtz & Volek PC

(57) ABSTRACT

In an apparatus and a method of evaluating a clamp force (F) in a threaded joint between a bolt and a matching threaded piece during a tightening operation, a torque (T) provided to the joint is continuously measured and ultra-sonic pulses are simultaneously induced into the bolt such that a time of flight (TOF) of the pulses in the bolt is measured. In response to an increase of the measured torque (T) an increase rate ($dT/d\alpha$) of the torque (T) is determined, from which an initial rotation angle ($\alpha_0$) where the torque (T) starts to increase due to bolt deformation is determined. An increase rate ($dTOF/d\alpha$) of the time of flight (TOF) is also determined. A total increase of the time of flight ($\Delta TOF$) during the tightening operation is then determined based on the initial rotation angle ($\alpha_0$) and the increase rate ($dTOF/d\alpha$) of the time of flight (TOF).

11 Claims, 2 Drawing Sheets

(51) Int. Cl.
*G01L 1/25* (2006.01)
*B25B 23/147* (2006.01)
*G01L 5/00* (2006.01)

(56) References Cited

U.S. PATENT DOCUMENTS

| | | | |
|---|---|---|---|
| 6,354,152 B1* | 3/2002 | Herlik | G01N 29/223 73/597 |
| 8,683,869 B2* | 4/2014 | Herley | G01L 5/246 73/760 |
| 8,810,370 B2* | 8/2014 | Tillotson | H04Q 9/00 340/10.1 |
| 9,021,896 B2* | 5/2015 | Carlin | B25B 21/02 73/862.21 |
| 2003/0011275 A1* | 1/2003 | Nasrollahzadeh | H01L 41/042 310/311 |
| 2006/0137463 A1 | 6/2006 | Nassar et al. | |
| 2006/0144157 A1 | 7/2006 | Kibblewhite et al. | |
| 2012/0222485 A1* | 9/2012 | Stickel | G01L 5/246 73/632 |
| 2013/0192389 A1* | 8/2013 | Carlin | B25B 21/02 73/862.21 |

* cited by examiner

METHOD AND APPARATUS FOR EVALUATING CLAMP FORCE IN A BOLT BY MEANS OF ULTRA-SONIC MEASUREMENTS

The invention relates to a method of performing ultra-sonic measurements of the clamp force in a bolt during tightening of a joint including said bolt, and to a tightening apparatus that implements said method.

BACKGROUND

When a joint between a bolt and a nut is tightened a clamp force is produced, which will keep the joint tightened. The clamp force is produced as a result of that a so called clamp length of the bolt is deformed, i.e. elongated. Generally, a tightening operation may be divided into two main phases; a first phase in which the bolt is threaded into the nut without deformation, and a second phase in which the joint between e.g. the bolt and a nut is established, and in which the bolt is being deformed. The bolt may be both elastically and plastically deformed. The transition point at which the threading phase ends and the deformation phase starts is conventionally denoted as snug.

In order to optimize a tightening operation it is desired to control the clamp force which is produced in the joint. It is however difficult to measure the clamp force directly, since that would imply having to place a force meter inside the joint, which is rarely possible. Instead, methods have been developed to measure the clamp force indirectly. One such method involves the use of ultra-sound to measure the elongation of the bolt. In other methods the joint is tightened to a certain torque instead of to a certain clamp force.

In the ultra sound method ultra-sonic pulses are transmitted into the bolt and the response time, often referred to as the time of flight, is monitored. The time of flight corresponds to the length of the bolt. Hence, any measured increase in the time of flight corresponds to an increase of the length of the bolt, and thus, of the clamp force in the bolt. The time of flight increases linearly with the elongation of the bolt, at least as long as the bolt is only elastically deformed. However, if the bolt is deformed to an extent that it starts to deform plastically, which is desired in certain applications, a new linearity will be established. Normally, the time of flight increases at a slower rate during the plastic deformation than during the elastic deformation.

A problem in the ultra sound method concerns the evaluation of the measured results. To start with, it is difficult to measure the time of flight in the bolt in a cost and time efficient manner before snug has been reached in the tightening operation. This is partly due to the fact that it is difficult to establish a good enough contact between the ultra-sonic meter and the bolt before the bolt has been clamped, e.g. before snug. After snug the bolt will be clamped in the joint and it will be much easier to achieve a good contact between the ultra-sonic meter and the bolt.

A conventional way of achieving a good contact is to incorporate a contact piece and an ultra-sonic pulse generator, e.g. in the form of a piezo-electric component in the head of the bolt. This is however a very costly solution and such a bolt will cost at least 20 times the price of an ordinary bolt.

SUMMARY OF THE INVENTION

An object of the invention is to provide a cost and time efficient way of evaluating measurements of time of flight in a bolt during the tightening of a joint.

This object is achieved by the invention according to a first and a second aspect.

According to the first aspect the invention relates to a method of evaluating the clamp force in a threaded joint between a bolt and a matching threaded piece during a tightening operation, which method includes the steps of:
tightening the joint by means of a torque delivering device,
measuring a torque provided to the joint during tightening thereof, and
simultaneously inducing ultra-sonic pulses into the bolt and measuring the time of flight (TOF) of said pulses in said bolt. The method further involves the steps of:
in response to a measured increase of the torque, monitoring the torque as a function of the rotation angle in order to determine an increase rate of the torque,
monitoring the time of flight of the ultra-sonic pulses as a function of the rotation angle, in order to determine an increase rate of the time of flight,
based on the determined increase rate of the torque, determining an initial rotation angle of the tightening operation where the torque starts to increase as a function of bolt deformation,
defining said initial rotation angle of the tightening operation as a rotation angle where the time of flight starts to increase, and
determining the total increase of the time of flight during the tightening operation based on said initial rotation angle of the tightening operation and said increase rate of the time of flight.

According to the second aspect the invention relates to a tightening apparatus for tightening joints including at least one bolt and a matching threaded piece, comprising a torque delivering device that includes:
a shaft for driving a tool implement in order to provide a mutual rotation to the bolt and the matching threaded piece, and
a motor for driving said shaft,
wherein the tightening apparatus further comprises:
a torque meter for measuring the torque as a function of the rotation angle applied to the joint between the bolt and the matching threaded piece during a tightening operation of said joint,
an ultra-sonic transmitter for inducing ultra-sonic pulses into the at least one bolt and measuring the time of flight of said pulses in said bolt,
a rotation angle meter for registering a rotation angle ($\alpha$) between the at least one bolt and the matching threaded piece during tightening of said joint,
characterised in that the tightening apparatus comprises a control unit that is adapted to:
determine an increase rate of the torque as a function of the rotation angle based on the measured torque,
determine an increase rate of the time of flight as a function of the rotation angle based on the measured time of flight,
based on the determined increase rate of the torque, determine an initial rotation angle where the torque starts to increase due to bolt deformation,
defining said initial rotation angle as the rotation angle where the time of flight starts to increase,
determine the total increase of the time of flight during the tightening operation based on said initial rotation angle and on said increase rate of the time of flight.

In a specific embodiment of the invention the invention the step of determining the increase rate of the torque comprises the steps of monitoring a first momentary torque at a first specific rotation angle of the tightening operation, and a subsequent second momentary torque at a second specific rotation angle of the tightening operation and performing a linear approximation thereof, and wherein the initial rotation angle is extrapolated from said linear approximation and correspond to the angle where the torque equals zero.

In another embodiment of the invention the step of determining the increase rate of the time of flight of the ultra-sonic pulses comprises the steps of monitoring a first momentary time of flight at a first related rotation angle of the tightening operation, and a subsequent second momentary time of flight at a second related rotation angle of the tightening operation and performing a linear approximation thereof.

In yet another embodiment of the invention an established clamp force in the joint is evaluated based on the total increase of the time of flight, the clamp force being presumed to be proportional to the total increase of the time of flight according to the equation $F=k_1*\Delta TOF$, where $k_1$ is a bolt specific constant dependent on the geometry and material of the bolt.

In one embodiment of the invention, subsequent to the calculation of the clamp force, the tightening operation is controlled to be terminated at a predetermined target clamp force, and wherein the total increase of time of flight is continuously monitored and the clamp force is continuously calculated from the monitored increase of time of flight.

In another embodiment of the invention the tightening operation is controlled to be terminated at a predetermined target torque, and wherein the total increase of time of flight is monitored such that a the clamp force may by calculated from the monitored total increase of time of flight when the predetermined target torque is met and the tightening operation is terminated.

In yet another embodiment of the invention the tightening operation is paused at the first related rotation angle of the tightening operation, at which the first momentary value of the time of flight of the ultra-sonic pulses is measured.

All the specific embodiments of the invention may either be implemented in the inventive method or in the inventive tightening apparatus as specific steps that the control unit may be adapted to perform.

Other features and advantages of the invention will be apparent from the figures and from the detailed description of the shown embodiment.

SHORT DESCRIPTION OF THE DRAWINGS

In the following detailed description reference is made to the accompanying drawings, of which:

DETAILED DESCRIPTION OF THE SHOWN EMBODIMENT OF THE INVENTION

Figure 1:
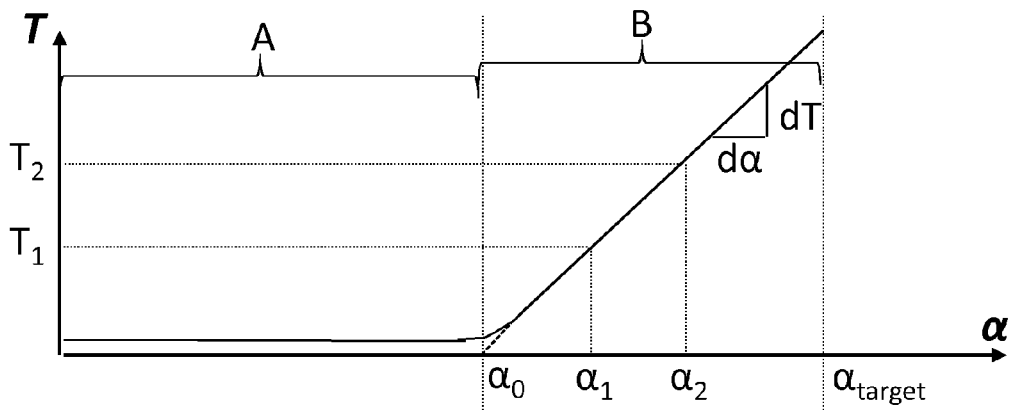
FIG. 1 is diagram illustrating the torque T as a function of the mutual rotation angle α of the bolt and the matching threaded piece during a tightening operation.

In FIG. 1 a diagram illustrating a tightening operation in accordance with the invention is shown. The diagram shows the torque T as a function of the rotation angle α between a first and a second threaded piece during a tightening operation of a joint comprising said first and second threaded piece.

Figure 3:
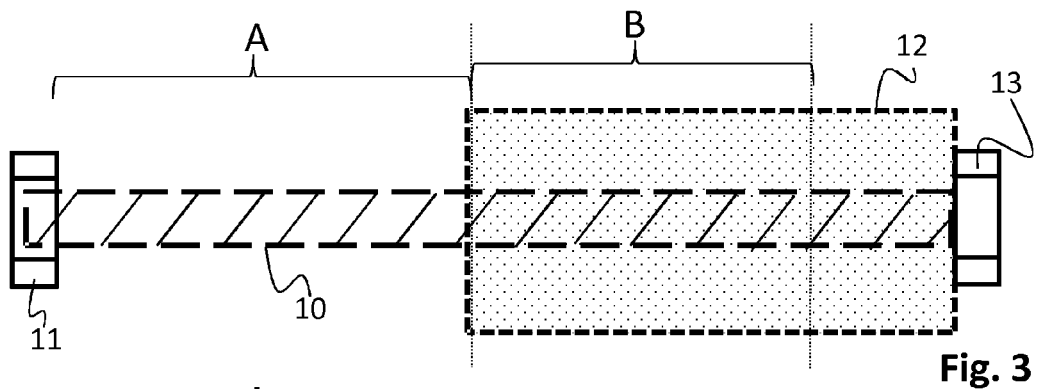
FIG. 3 shows a bolt and a nut in an initial position of a threading operation.
Figure 4:
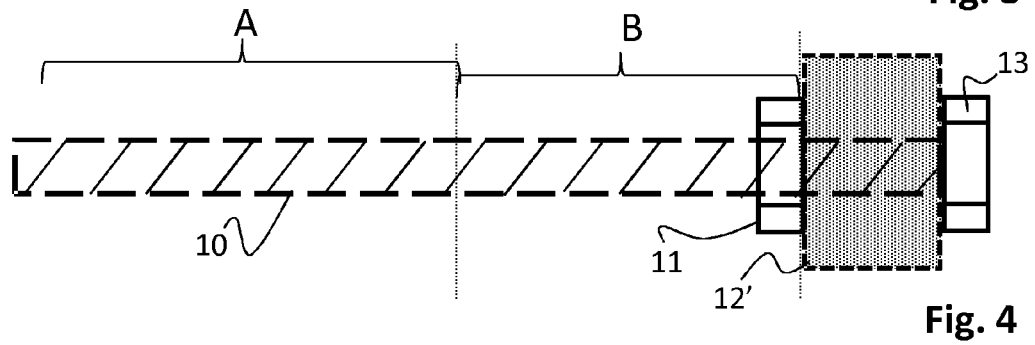
FIG. 4 shows the bolt and the nut in FIG. 3 when the nut has been securely clamped to the bolt.

The joint is exemplified by a bolt 10 and a nut 11 in FIGS. 3 and 4. In the example the nut 11 is screwed onto the bolt 10 so as to clamp a spongy piece 12 in between them. This illustration is a simplification of an actual tightening operation meant to illustrate the variation of the torque T and the clamp force F as a function of the rotation angle α. In FIG. 3, the nut 11 is at the loose and of the bolt 12, and in in FIG. 4 the nut 11 has been threaded all the way to the target rotation angle $\alpha_{target}$ that corresponds to a desired target clamp force $F_{target}$.

As is visible in the diagram of FIG. 1 the torque T is close to zero during an initial phase A of the tightening operation, when the nut 11 is threaded onto the bolt 10. During this first phase A the torque T is only dependent on the friction between the bolt 10 and the nut 11. Once the nut 11 has been screwed into contact with the spongy piece 12, i.e. at rotation angle $\alpha_0$, further movement of the nut 11 will compress the spongy piece 12, such that the torque T will start to increase. In a subsequent second phase B of the tightening the spongy piece 12 functions as a perfect spring, such that its active "spring force" will increase linearly in proportion to its compression. Hence, the clamp force F in the joint will increase linearly as a function of the rotation angle α during the second phase B of the tightening operation. The clamp force F is in the exemplary embodiment provided in that a waist (not shown) between the head 13 of the bolt 10 will be elastically extended as a result of the increased pressure from the spongy piece 12 that acts on the head 13 of the bolt 10. The clamp force F will be equally big as, but opposed to, the spring force of the spongy piece 12.

Now, with reference to FIG. 1, the torque T needed to turn the nut 11 with respect to the bolt 10 will also increase linearly during the second phase B of the tightening operation, as the torque T is proportional to the axial force and to the screw pitch of the bolt 10. In the shown example the screw pitch of the bolt 10 is the same along the whole length of the bolt 10, such that the torque T will be linearly proportional to the axial force provided by the spring force of the spongy piece 12 along the whole length of the bolt 10.

The torque T may be continuously monitored by means of a torque meter included in a torque delivering device. The torque delivering device may be a torque wrench or a power tool, such as e.g. a nut runner. It is possible to control the tightening towards a specific target torque $T_{target}$, which is conventional in the art. Normally though, it is desired to achieve a certain target clamp force $F_{target}$ in a joint instead of a specific target torque $T_{target}$. A problem is, however, that it is not possible to measure the clamp force F directly by means of the torque delivering device. Instead the clamp force F is either estimated from the measured torque T or measured indirectly, e.g. by means of ultra-sonic pulses.

In the present invention, the clamp force F is measured indirectly by measuring the time of flight TOF of ultra-sonic pulses inside the bolt 10. The time of flight TOF of the ultra-sonic pulses corresponds to time it takes for the ultra-sonic pulses to travel through the bolt 10 and back. Hence, the time of flight TOF indicates the length of the bolt. Hence, the total increase of the time of flight ΔTOF corresponds to the extension of the elastic portion of the bolt according to a known relationship, which is dependent on the geometry and composition of the bolt. In reality, the total increase of the time of flight ΔTOF does not only depend on the extension of the bolt. In addition it is also dependent of induced tensions in the bolt 10, such that an increased tension in the material yields an increased time of flight TOF for the ultra-sonic pulses. The relationship of how much of the total increase of the time of flight $\Delta$TOF that corresponds to the increased tension in the material or to the extension of the bolt, respectively, is bolt specific and may have to be empirically tested for each specific bolt type, but it does not need to be tested for each bolt of a specific type. Typically, a third of the total increase of the time of flight $\Delta$TOF corresponds to the actual extension of the bolt, and the remaining two thirds correspond to the increased tensions in the material.

Figure 2:
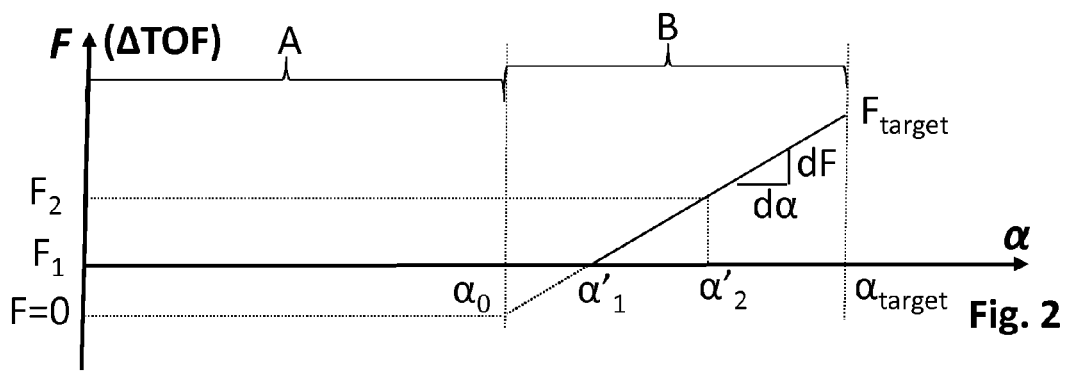
FIG. 2 is diagram illustrating the clamp force F as a function of the mutual rotation angle α of the bolt and the matching threaded piece during a tightening operation.

In FIG. 2, the clamp force F in a joint is shown as a function of the mutual rotation angle between a first and a second threaded piece during a tightening operation. The clamp force F is directly proportional to the total increase of the time of flight $\Delta$TOF. A problem in the measuring of the time of flight TOF is that is not evident to know the total increase of the time of flight $\Delta$TOF, because it is difficult to determine the rotation angle where the time of flight $\Delta$TOF starts to increase. This is due to that is difficult to establish the needed, solid connection between the ultra-sonic transmitter and the head of the bolt, when the bolt is being screwed at a low torque.

As a consequence, the first measured value of the time of flight $TOF_1$ is measured at a rotation angle that corresponds to a first related rotation angle $\alpha'_1$, which is located beyond snug and inside the second phase B of the tightening operation. Namely, at this rotation angle, connection has been accomplished between the ultra-sonic transmitter and the head of the bolt. In a specific embodiment of the invention, the tightening operation may even be paused for a moment to ensure that the first measured value of the time of flight $TOF_1$ will be correctly measured. The first measured value of the time of flight $TOF_1$ corresponds to the clamp force $F_1$ at the first related rotation angle $\alpha'_1$. At this point it will hence not be possible to correctly evaluate the actual clamp force $F_1$. This is, as indicated above, due to the fact that the initial time of flight $TOF_0$ that corresponds to the length of the bolt 10 before it has been deformed by elongation is not known. On the other hand, once the connection has been established it will be possible to continuously monitor the increase of the time of flight TOF and consequently the clamp force F. In other words, it will be possible to deduce an increase rate $dTOF/d\alpha$ of the time of flight TOF as a function of the rotation angle $\alpha$.

The invention presents a manner of finding the initial time of flight $TOF_0$ without having to measure it. Namely, by using the measurements of the torque T it is possible to deduce a starting rotation angle $\alpha_0$ of the elastic deformation of the bolt, since this starting rotation angle $\alpha_0$ corresponds to the rotation angle at which both the torque T and the clamp force F starts to increase linearly. The starting rotation angle $\alpha_0$ may be found by extrapolating the curve of the torque T as a function of the rotation angle $\alpha$. The starting rotation angle $\alpha_0$ is the rotation angle at which the elastic deformation of the bolt is initiated, and consequently the rotation angle where the torque T equals zero.

In a specific embodiment of the invention, the inventive method involves the following steps:

(1) In response to an increase in measured torque T, a first momentary torque $T_1$ is monitored at a first specific rotation angle $\alpha_1$, and a subsequent second momentary $T_2$ torque is monitored at a second specific rotation angle $\alpha_2$, in order to determine an increase rate $dT/d\alpha$ of the torque T.

(2) A first momentary value of the time of flight $TOF_1$ of the ultra-sonic pulses is monitored at a first related rotation angle $\alpha'_1$, and a subsequent second momentary value of the time of flight $TOF_2$ is monitored at a second related rotation angle $\alpha'_2$ in order to determine an increase rate $dTOF/d\alpha$ of the time of flight TOF. It is to be noted that the related rotation angles $\alpha'_1$, $\alpha'_2$ at which the time of flight TOF is monitored may, or may not, be the same as the specific rotation angles $\alpha_1$, $\alpha_2$, at which the torque T is measured. In FIG. 2, the clamp force F and not the time of flight TOF is illustrated as a function of the rotation angle $\alpha$. This is possible because the clamp force F is directly proportional to the total increase of the time of flight $\Delta$TOF. Hence, a curve showing the time of flight TOF as a function of the rotation angle $\alpha$ would be the same except for the slope of the curve and its position along the Y-axis. In the curve shown in FIG. 2 these differences are however not apparent as the axes are shown without magnitudes, such that neither the physical slope of the curve nor the position of the curve along the Y-axis is shown.

(3) An initial rotation angle $\alpha_0$ of the tightening operation is determined, at which the torque starts to increase as a function of the bolt deformation. In the shown example this is done by assuming that the curve is linear, such that the initial rotation angle $\alpha_0$ may be found by extrapolating the curve backwards from the two rotation angles $[\alpha_2, T_2]$ and $[\alpha_1, T_1]$. In other configurations of the invention the torque T may have another dependency with respect to the rotation angle $\alpha$. In most cases the torque T will however increase linearly with respect to the rotation angle $\alpha$, such that the increase rate $dT/d\alpha$ of the torque T will be constant.

(4) The initial rotation angle $\alpha_0$ of the tightening operation is defined as a rotation angle where the time of flight TOF starts to increase in order to determine the total increase of the time of flight $\Delta$TOF during the tightening operation. The clamp force F in the joint may be deduced directly from a bolt specific coefficient and the total increase of the time of flight $\Delta$TOF.

Figure 5:
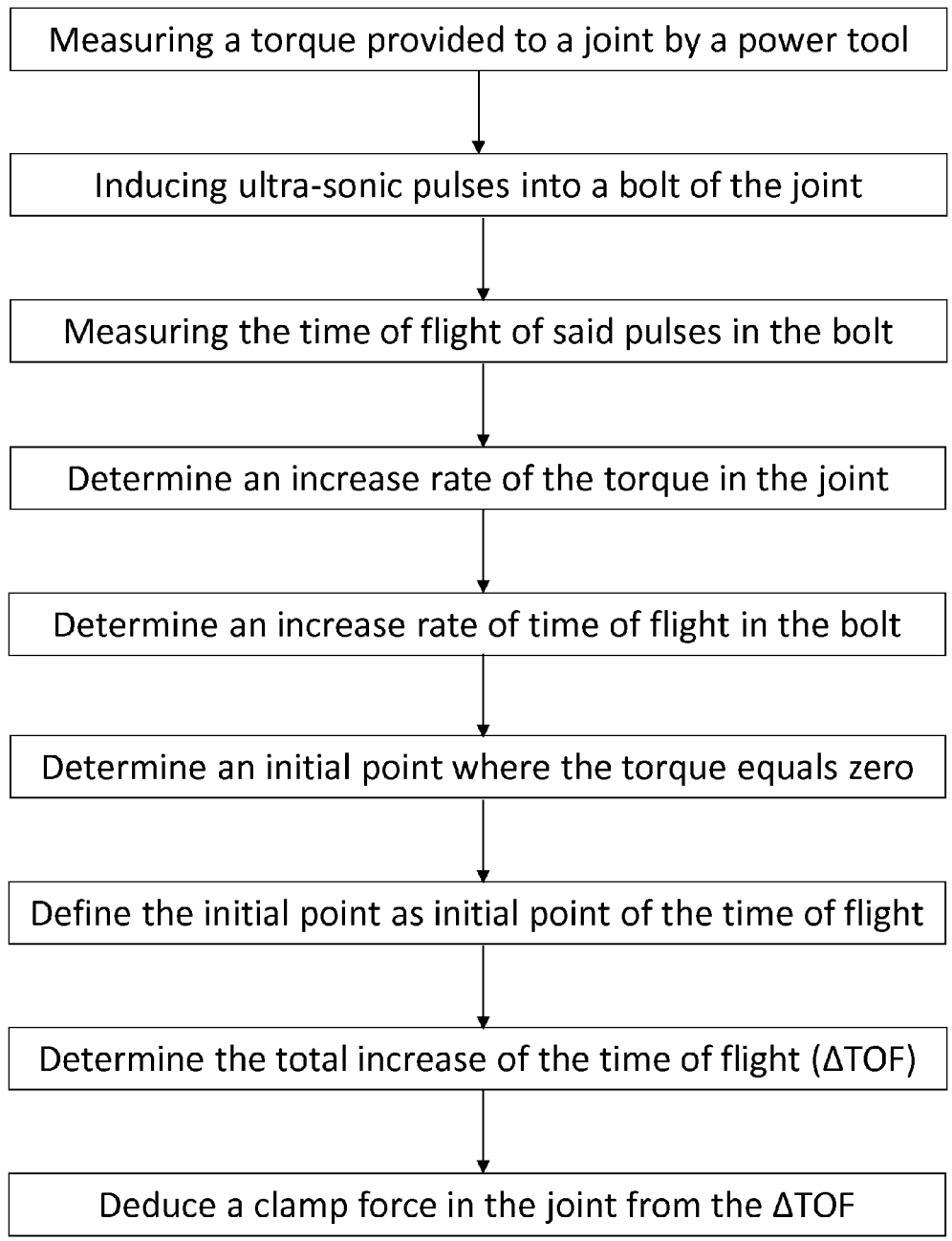
FIG. 5 shows a block diagram an embodiment of the method according to the invention.

From the above inventive method, the tightening operation may be controlled towards a specific target clamp force $F_{target}$. A specific embodiment of the inventive method is presented in FIG. 5. As is indicated in FIGS. 1 and 2, it is also possible to deduce a target rotation angle $\alpha_{target}$, at which the tightening operation should be terminated. The target rotation angle $\alpha_{target}$ may be determined without the step of defining the initial rotation angle $\alpha_0$ as the rotation angle where the time of flight TOF starts to increase. Instead, the clamp force F may be calculated based on the difference in the rates at which the torque T and clamp force F, respectively, increase as a function of the rotation angle $\alpha$, and on the momentary value of the torque T.

In a specific embodiment of the invention it suffices to monitor either the increase rate of either the time of flight TOF or the torque T as a function of the rotation angle $\alpha$. Namely, if both the increase rate $dTOF/d\alpha$ of the time of flight TOF and the increase rate $dT/d\alpha$ of the torque T as a function of the rotation angle $\alpha$ are known, it will be sufficient to know the torque T at one specific rotation angle $\alpha'$ in order to deduce the clamp force F from the momentary values of the time of flight TOF. This is possible, as it is known that the clamp force F is directly proportional to the time of flight TOF, according to the equation (1) $F=k_1*TOF$, where $k_1$ is a bolt specific constant that is dependent on the geometry and composition of the bolt. Further though, the clamp force F is proportional to the torque T, according to the equation (2) $F=k_2*T$, where $k_2$ equals the ratio of $dF/d\alpha$ divided by $dT/d\alpha$.

From the formulas above follows that it will be possible to deduce the clamp force $F_\alpha$ at an angle $\alpha$ from either a monitored torque value $T_\alpha$ or monitored values of the time of flight $TOF_\alpha$ at that specific angle $\alpha$. Hence, it will in principle be possible to conclude the tightening by either monitoring the time of flight TOF or the torque value T, and evaluating the clamp force F from either of the equations (1 or 2) above.

Regardless of which specific method is used, the target clamp force $F_{target}$ may be re-evaluated throughout the whole tightening operation. For instance, further specific rotation angles than the two needed to determine the slopes of the respective curves may be included to determine both the momentary clamp force F and the target clamp force $F_{target}$ as accurately as possible during the tightening operation.

Above, the invention has been described with reference to one specific embodiment. The invention is however not limited to this embodiment. It is obvious to a person skilled in the art that other embodiments are feasible within the scope of the invention, which is defined by the following claims.

The invention claimed is:

1. A method of evaluating a clamp force (F) in a threaded joint between at least one bolt and a matching threaded piece during a tightening operation, comprises:
   tightening the joint by means of a torque delivering device,
   registering a rotation angle ($\alpha$) between the at least one bolt and the matching threaded piece during tightening of the joint,
   measuring a torque (T) provided to the joint during tightening thereof,
   simultaneously inducing ultra-sonic pulses into the at least one bolt and measuring a time of flight (TOF) of the pulses in the at least one bolt,
   monitoring, in response to a measured increase of the torque (T), the torque (T) as a function of the rotation angle ($\alpha$) in order to determine an increase rate ($dT/d\alpha$) of the torque (T),
   monitoring a time of flight ($TOF_1$) of the ultra-sonic pulses as a function of the rotation angle ($\alpha$), in order to determine an increase rate ($dTOF/d\alpha$) of the time of flight (TOF),
   determining, based on the determined increase rate ($dT/d\alpha$) of the torque (T), an initial rotation angle ($\alpha_0$) of the tightening operation where the torque (T) starts to increase as a function of bolt deformation,
   defining the initial rotation angle ($\alpha_0$) of the tightening operation as a rotation angle where the time of flight (TOF) starts to increase,
   determining a total increase of the time of flight ($\Delta TOF$) during the tightening operation based on the initial rotation angle ($\alpha_0$) of the tightening operation and the increase rate ($dTOF/d\alpha$) of the time of flight (TOF), and
   evaluating an established clamp force (F) in the joint based on the total increase of the time of flight ($\Delta TOF$), the clamp force (F) being presumed to be proportional to the total increase of the time of flight ($\Delta TOF$) according to the equation $F=k_1*\Delta TOF$, where $k_1$ is a bolt specific constant dependent on the geometry and material of the bolt.

2. The method according to claim 1, wherein determining the increase rate ($dT/d\alpha$) of the torque (T) comprises monitoring a first momentary torque ($T_1$) at a first specific rotation angle ($\alpha_1$) of the tightening operation, and a subsequent second momentary torque ($T_2$) at a second specific rotation angle ($\alpha_2$) of the tightening operation, and performing a linear approximation thereof, and wherein the initial rotation angle ($\alpha_0$) is extrapolated from the linear approximation and corresponds to the angle where the torque (T) equals zero.

3. The method according to claim 2, wherein determining the increase rate ($dTOF/d\alpha$) of the time of flight (TOF) of the ultra-sonic pulses comprises monitoring a first momentary time of flight ($TOF_1$) at a first related rotation angle ($a'_1$) of the tightening operation, and a subsequent second momentary time of flight ($TOF_2$) at a second related rotation angle ($a'_2$) of the tightening operation and performing a linear approximation thereof.

4. The method according to claim 3, wherein the tightening operation is paused at the first related rotation angle ($\alpha'_1$) of the tightening operation, at which the first momentary value of the time of flight ($TOF_1$) of the ultra-sonic pulses is measured.

5. The method according to claim 1, wherein determining the increase rate ($dTOF/d\alpha$) of the time of flight (TOF) of the ultra-sonic pulses comprises monitoring a first momentary time of flight ($TOF_1$) at a first related rotation angle ($\alpha'_1$) of the tightening operation, and a subsequent second momentary time of flight ($TOF_2$) at a second related rotation angle ($\alpha'_2$) of the tightening operation and performing a linear approximation thereof.

6. The method according to claim 5, wherein the tightening operation is paused at the first related rotation angle ($\alpha'_1$) of the tightening operation, at which the first momentary value of the time of flight ($TOF_1$) of the ultra-sonic pulses is measured.

7. The method according to claim 1, wherein, subsequent to the calculation of the clamp force (F), the tightening operation is controlled to be terminated at a predetermined target clamp force ($F_{target}$), and wherein the total increase of time of flight ($\Delta TOF$) is continuously monitored and the clamp force (F) is continuously calculated from the monitored increase of time of flight ($\Delta TOF$).

8. The method according to claim 7, wherein the tightening operation is paused at the first related rotation angle ($\alpha'_1$) of the tightening operation, at which the first momentary value of the time of flight ($TOF_1$) of the ultra-sonic pulses is measured.

9. The method according to claim 1, wherein the tightening operation is controlled to be terminated at a predetermined target torque ($T_{target}$), and wherein the total increase of time of flight ($\Delta TOF$) is monitored such that the clamp force (F) may by calculated from the monitored total increase of time of flight ($\Delta TOF$) when the predetermined target torque ($T_{target}$) is met and the tightening operation is terminated.

10. The method according to claim 9, wherein the tightening operation is paused at the first related rotation angle ($\alpha'_1$) of the tightening operation, at which the first momentary value of the time of flight ($TOF_1$) of the ultra-sonic pulses is measured.

11. A tightening apparatus for tightening at least one joint between at least one bolt and a matching threaded piece, comprising:
   a torque delivering device that comprises:
      a shaft for driving a tool implement in order to provide a mutual rotation to the at least one bolt and the matching threaded piece, and
      a motor for driving the shaft,
   a torque meter for measuring the torque as a function of a rotation angle applied to the at least one joint between the at least one bolt and the matching threaded piece during a tightening operation of the at least one joint, an ultra-sonic transmitter for inducing ultra-sonic pulses into the at least one bolt and measuring a time of flight (TOF) of the pulses in the at least one bolt, a rotation angle meter for registering a rotation angle ($\alpha$) between the at least one bolt and the matching threaded piece during tightening of the at least one joint, and a control unit configured to:

determine an increase rate ($dT/d\alpha$) of a torque (T) as a function of the rotation angle ($\alpha$) based on the measured torque (T), determine an increase rate ($dTOF/d\alpha$) of the time of flight (TOF) as a function of the rotation angle ($\alpha$) based on the measured time of flight (TOF), determine, based on the determined increase rate ($dT/d\alpha$) of the torque (T), an initial rotation angle ($\alpha_0$) where the torque (T) starts to increase due to bolt deformation, defining the initial rotation angle ($\alpha_0$) as the rotation angle where the time of flight (TOF) starts to increase, determine a total increase of the time of flight ($\Delta TOF$) during the tightening operation based on the initial rotation angle ($\alpha_0$) and on the increase rate ($dTOF/d\alpha$) of the time of flight (TOF), and evaluate an established clamp force (F) in the at least one joint based on the total increase of the time of flight ($\Delta TOF$), the clamp force (F) being presumed to be proportional to the total increase of the time of flight ($\Delta TOF$) according to the equation $F=k_1*\Delta TOF$, where $k_1$ is a bolt specific constant dependent on the geometry and material of the bolt.

\* \* \* \* \*